(12) United States Patent
Steckelings et al.

(10) Patent No.: US 8,835,471 B2
(45) Date of Patent: Sep. 16, 2014

(54) USE OF ANGIOTENSIN II AGONISTS

(75) Inventors: Ulrike Steckelings, Berlin (DE);
Thomas Unger, Berlin (DE)

(73) Assignee: Vicore Pharma AB

( * ) Notice: Subject to any disclaimer, the term of this patent is extended or adjusted under 35 U.S.C. 154(b) by 288 days.

(21) Appl. No.: 13/157,262

(22) Filed: Jun. 9, 2011

(65) Prior Publication Data
US 2012/0035232 A1 Feb. 9, 2012

Related U.S. Application Data

(60) Provisional application No. 61/353,808, filed on Jun. 11, 2010.

(51) Int. Cl.
*A61K 31/44* (2006.01)
*C07D 233/62* (2006.01)
*A61K 31/4178* (2006.01)

(52) U.S. Cl.
CPC .................................. *A61K 31/4178* (2013.01)
USPC ......... 514/365; 514/385; 548/202; 548/315.1

(58) Field of Classification Search
USPC ........................ 548/202, 315.1; 514/365, 385
See application file for complete search history.

(56) References Cited

FOREIGN PATENT DOCUMENTS

| GB | 2 281 298 A | 3/1995 |
|---|---|---|
| WO | WO 99/43339 | 3/1999 |
| WO | WO 02/096883 | 12/2002 |

OTHER PUBLICATIONS

Wan et al, Design, Synthesis and Biological Evaluation of the First Selective Nonpeptide AT2 Receptor Agonist, J. Med. Chem. (2004), vol. 47, pp. 5995-6008.*
Wu et al, "Selective Angiotensin II AT2 Receptor Agonists," J. Med. Chem. (2006), vol. 49, pp. 7160-7168.*
Reinecke, K. et al., "Angiotensin H Accelerates Functional Recovery In the Rat Sciatic Nerve in Vivo: Role of the AT2 Receptor and the Transcription Factor NF-KB1," FASEB J., 17(14): 2094-6 (2003).*
Audiomedica.com web page titled "Angiotensin AT2 Receptor Agonist: Restorative Role for Patients with Hypertension?" (Jun. 29, 2009).
Ardaillou, Raymond, "Angiotensin II Receptors," J. Am. Soc. Nephrol. 10:S30-S39 (1999).
Basso, D.M. et al., "Basso Mouse Scale for Locomotion Detects Differences in Recovery after Spinal Cord Injury in Five Common Mouse Strains," Journal of Neurotrauma vol. 23. No. 5, 635-659 (2006).
Bottai D. et al., "Embryonic Stem Cells Promote Motor Recovery and Affect Inflammatory Cell Infiltration in Spinal Cord Injured Mice," Experimental Neurology, 223, 452-463 (2010).
De Gasparo, M. et al., "International Union of Pharmacology, XXIII. The Angiotensin II Receptors," Pharmacolocical Reviews. 52, 415-472 (2000).
Kingwell, K., "BDNF Copycats," Nature Reviews Drug Discovery, 9, 433 (2010).
Lucius, R. et al., "The Angiotensin II Type 2 ($AT_2$) Receptor Promotes Axonal Regeneration in the Optic Nerve of Adult Rats," J. Exp. Med, 188(4), 661-670 (1998).
Massa, S.M. et al., "Small Molecule BDNF Mimetics Activate TrkB Signaling and Prevent Neuronal Degenerations in Rodents," J. Clin. Invest., 120, 1774-1785 (2010).
Nakajima, H. MD, Ph. D., et al., "Targeted Retrograde Gene Delivery of Brain-Derived Neurotrophic Factor Suppresses Apoptosis of Neurons and Oligodendroglia After Spinal Cord Injury in Rats," SPINE 35(5), 497-504 (2010).
Reinecke, K. et al., "Angiotensin II Accelerates Functional Recovery in the Rat Sciatic Nerve In Vivo: Role of the $AT_2$ Receptor and the Transcription Factor NF-κB[1]," FASEB J., 17(14): 2094-6 (2003).
Reinecke, K. et al., "Angiotensin II Accelerates Functional Recovery in the Rat Sciatic Nerve In Vivo: Role of the $AT_2$ Receptor and the transcription Factor NF-κB[1]," FASEB J. express article 10.1096/fj. 02-1193je. Published online Sep. 18, 2003.
Sayer, F.T. et al., "Neurotrophins Reduce Degeneration of Injured Ascending Sensory and Corticospinal Motor Axons in Adult Rat Spinal Cord," Experimental Neurology, 175 282-296 (2002)
Tanaka E.M. et al., "Considering the evolution of Regeneration in the Centeral Nervous System," Nature Reviews Neuroscience, 10, 713-723 (2009).
Wan. Y. et al., "Design, Synthesis and Biological Evaluation of the First Selective Nonpeptide $AT_2$ Receptor Agonist," J. Med. Chem., 47, 5995-6008 (2004).
"AT2 Receptor Stimulation—cardiorenal and neuronal aspects," presentation by Thomas Unger at The 19th European Meeting on Hypertension in Milan (2009), Jun. 12-Jun. 16, 2009.
Boato, Francesco et al., "C3 peptide enhances recovery from spinal cord injury by improved regenerative growth of descending fiber tracts," Journal of Cell Science (2010) 123, 1652-1662.

* cited by examiner

*Primary Examiner* — Kamal Saeed
*Assistant Examiner* — Janet L Coppins
(74) *Attorney, Agent, or Firm* — Finnegan, Henderson, Farabow, Garrett & Dunner, LLP

(57) ABSTRACT

There is provided a compound of formula I,

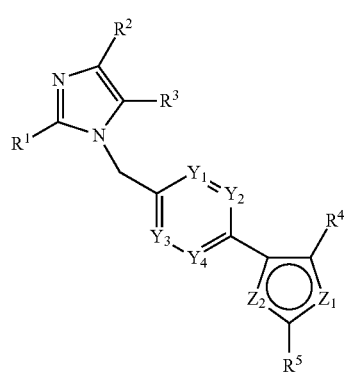

wherein $Y_1$, $Y_2$, $Y_3$, $Y_4$, $Z_1$, $Z_2$, $R^1$, $R^2$, $R^3$, $R^4$ and $R^5$ have meanings given in the description, and pharmaceutically-acceptable salts thereof, for use in the treatment of spinal cord injury.

18 Claims, 8 Drawing Sheets

BDNF

TrkB

Nissl staining in the core

USE OF ANGIOTENSIN II AGONISTS

Figure 1:
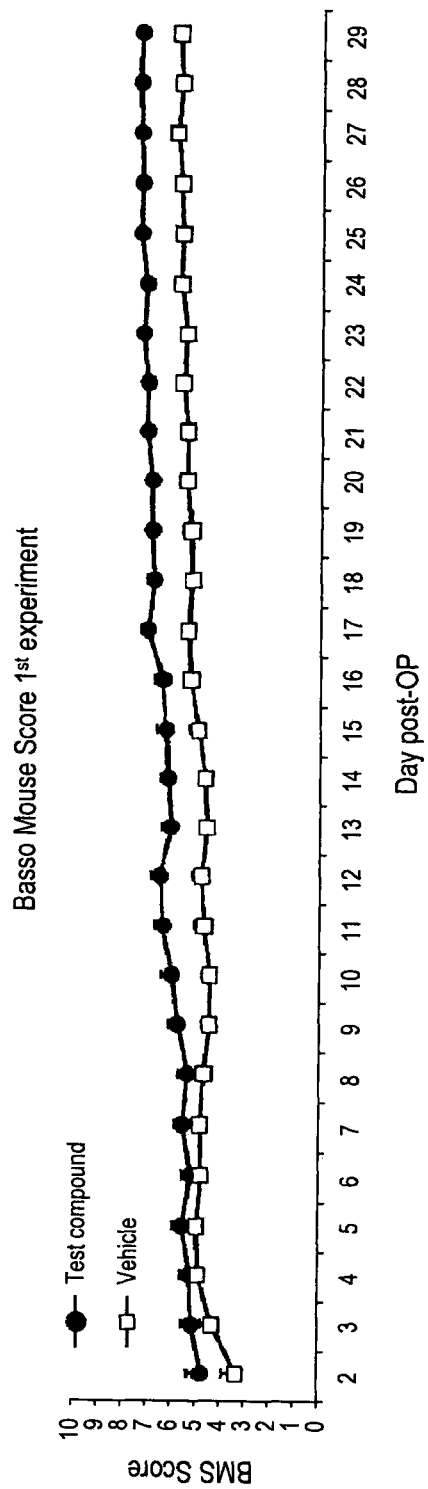

This patent application claims the benefit of U.S. provisional application No. 61/353,808, filed Jun. 11, 2010, which is incorporated herein by reference.

FIELD OF THE INVENTION

This invention relates to a new use of compounds that are angiotensin II (AngII) agonists, more particularly agonists of the AngII type 2 receptor (hereinafter the AT2 receptor), and especially agonists that bind selectively to that receptor.

BACKGROUND

Spinal cord injury involves damage to nerve roots or myelinated fibre tracts that carry signals to and from the brain.

The consequences of a spinal cord injury may vary depending on the type, level, and severity of injury, but can be classified into two general categories: complete injury and incomplete injury.

In a complete injury, function below the "neurological" level is lost. Absence of motor and sensory function below a specific spinal level is considered a "complete injury". Recent evidence suggests that less than 5% of people with "complete" spinal cord injuries recover locomotion.

In an incomplete injury, some sensation and/or movement below the level of the injury is retained. For example, when the ability to contract the anal sphincter voluntarily or to feel peri-anal pinprick or touch is retained, the injury is considered to be "incomplete".

In addition to loss of sensation and motor function below the level of injury, individuals with spinal cord injuries will also often experience other complications (e.g. dysfunction of the bowel and bladder; sexual dysfunction; loss of breathing; inability or reduced ability to regulate heart rate, blood pressure, sweating and hence body temperature; spasticity; neuropathic pain; autonomic dysreflexia; atrophy of muscle; Superior Mesenteric Artery Syndrome; osteoporosis and bone degeneration; and gallbladder and renal stones).

Current treatment for spinal cord injuries involves the short-term use of anti-inflammatory drugs. However, this may not reduce the paralysing effects of injury or promote re-growth of functional nerve fibres. There is a need for new and improved methods of regenerating neuronal tissue, in particular, reinnervation or remyelination, in such situations.

It is known that certain neurotrophic factors may be used to promote neurite outgrowth in vitro (Sayer F. T., et al., *Experimental Neurology*, (2002) 175 282-296) however, neurite outgrowth is not a marker for regeneration, but is rather a marker for differentiation. With reference to Tanaka et al., *Nature Reviews Neuroscience*, 10, 713-723 (2009), the term regeneration requires re-acquiring neuronal function; this obviously is not possible to show in vitro, e.g. in the neurite outgrowth assays. Following spinal cord injury, local expression of various neurotrophic factors (including brain-derived neurotrophic factor, BDNF) decreases, and it has been shown that treatment with neurotrophins promotes regeneration.

Exogenous administration of BDNF has also been shown to promote neural cell survival, alleviate neuronal atrophy, facilitate axonal regeneration, prevent apoptosis, enhance differentiation of neuronal stem cells to neurons followed by improvement of motor functions, and induce glial cell proliferation, axonal outgrowth and myelination (Nakajima H., et al., *SPINE*, 35(5), 497-504 (2010).

Activation of tropomyosin-related kinase (Trk) receptors (e.g. by BDNF which acts through the TrkB receptor) has been shown to promote neuronal cell survival, differentiation and synaptic function (Massa S. M., et al., *J. Clin. Invest.*, 120, 1774-1785 (2010)).

Certain small molecules have been shown to be capable of mimicking BDNF by activating TrkB signalling (Massa S. M., supra). However these small molecules were not shown to be agonists of the AT2 receptor.

The endogenous hormone AngII is a linear octapeptide ($Asp^1$-$Arg^2$-$Val^3$-$Tyr^4$-$Ile^5$-$His^6$-$Pro^7$-$Phe^8$), and is the active component of the renin-angiotensin system (RAS). It is produced by the sequential processing of the pro-hormone angiotensinogen by renin and angiotensin converting enzyme (ACE).

The renin-angiotensin system (RAS) plays an important role in the regulation of blood pressure, body fluid and electrolyte homeostasis. AngII exerts these physiological actions in many organs including the kidneys, the adrenal glands, the heart, blood vessels, the brain, the gastrointestinal tract and the reproductive organs (de Gasparo et al, *Pharmacol. Rev.* (2000) 52, 415-472).

Two main classes of AngII receptors have been identified, and designated as the type 1 receptor (hereinafter the AT1 receptor) and the AT2 receptor. The AT1 receptor is expressed in most organs, and is believed to be responsible for the majority of the biological effects of AngII. The AT2 receptor is more prevalent than the AT1 receptor in fetal tissues, the adult ovaries, the adrenal medulla and the pancreas. An equal distribution is reported in the brain and uterus (Ardaillou, *J. Am. Soc. Nephrol.*, 10, S30-39 (1999)).

Several studies in adult individuals appear to demonstrate that, in the modulation of the response following AngII stimulation, activation of the AT2 receptor has opposing effects to those mediated by the AT1 receptor.

The AT2 receptor has also been shown to be involved in apoptosis and inhibition of cell proliferation (see de Gasparo et al, supra). Further, it seems to play a role in blood pressure control. For example, it has been shown in transgenic mice lacking AT2 receptors that their blood pressure was elevated. Furthermore, it has been concluded that the AT2 receptor is involved in exploratory behaviour, pain sensitivity and thermoregulation.

The expression of AT2 receptors has also been shown to occur upon tissue injury in the nervous system after central nervous system lesion (Lucius et al., *J. Exp. Med.*, 188(4), 661-670 (1998).

The expected pharmacological effects of agonism of the AT2 receptor are described generally in de Gasparo et al, supra. It is not mentioned that agonism of the AT2 receptor may be used to treat spinal chord injury.

More recently, AT2 receptor agonists have been shown to be of potential utility in the treatment and/or prophylaxis of disorders of the alimentary tract, such as dyspepsia and irritable bowel syndrome, as well as multiple organ failure (see international patent application WO 99/43339).

Studies have shown that stimulation of the AT2 receptor with AngII promotes axonal regeneration in postnatal retinal explants and dorsal root ganglia in vitro as well as after optic nerve crush in vivo (Lucius et al., supra.). Although AngII is non-selective (i.e. it does not selectively bind to one or more angiotensin receptors in preference to the others) this study showed that it is the binding of AngII to the AT2 receptor that is important in the promotion of axonal regeneration in the model studied.

Studies have also shown that stimulation of the AT2 receptor with AngII promotes neuronal regeneration and functional recovery in rats following damage to their sciatic nerve in vivo (Reinecke K., et al., *FASEB J.* 2003 17: 2094-2096).

AT2 receptor agonists have also been described in the prior art, for instance in international patent application WO 2002/096883. However, the use of those compounds in the treatment of spinal cord injury is not mentioned. Further, there is no indication that the compounds are capable of mimicking BDNF and activating TrkB signalling in vivo.

The listing or discussion of an apparently prior-published document in this specification should not necessarily be taken as an acknowledgement that the document is part of the state of the art or is common general knowledge.

DISCLOSURE OF THE INVENTION

According to a first aspect of the invention, there is provided an AT2 receptor agonist (or a compound capable of stimulating AT2 receptors), or a pharmaceutically acceptable salt thereof, for use in the treatment of spinal cord injury. Such AT2 receptor agonists (or compounds capable of stimulating AT2 receptors) may be referred to herein as the "compounds of the invention".

According to a second aspect of the invention, there is provided the use of an AT2 receptor agonist (or a compound capable of stimulating AT2 receptors), or a pharmaceutically acceptable salt thereof, in the treatment of spinal cord injury.

In another aspect of the invention, compounds which are either AT2 receptor agonists or which are capable of stimulating AT2 receptors, or pharmaceutically acceptable salts thereof, may also be used in the manufacture of a medicament for the treatment of spinal cord injury.

According to a third aspect of the invention, there is provided a method of treating spinal cord injury, which method comprises the administration of an AT2 receptor agonist (or a compound capable of stimulating AT2 receptors), or a pharmaceutically acceptable salt thereof, to a patient in need of such therapy.

Preferred AT2 receptor agonists include those that bind selectively to the AT2 receptor.

Further preferred AT2 receptor agonists include compounds of formula I,

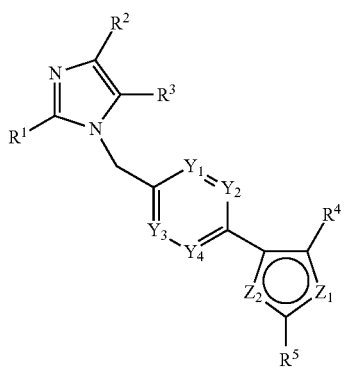

I wherein
$R^1$ represents H;
$R^2$ and $R^3$ independently represent H, $C_{1-6}$ alkyl, $C_{1-6}$ alkoxy, $C_{1-6}$ alkoxy-$C_{1-6}$-alkyl or halo;
$Y_1$, $Y_2$, $Y_3$ and $Y_4$ independently represent —CH— or —CF—;
$Z_1$ represents —S—;
$Z_2$ represents —CH— or —N—;
$R^4$ represents —S(O)$_2$N(H)C(O)R$^6$, —S(O)$_2$N(H)S(O)$_2$R$^6$, —C(O)N(H)S(O)$_2$R$^6$;

$R^5$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl; and
$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino;

or a pharmaceutically-acceptable salt thereof,
which compounds and salts are also referred to together hereinafter as "the compounds of the invention".

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example using a suitable ion exchange resin. For the avoidance of doubt, other pharmaceutically acceptable derivatives of compounds of the invention are included within the scope of the invention (e.g. solvates, etc).

Unless otherwise specified, alkyl groups, and the alkyl parts of alkoxy, alkoxyalkyl, alkoxyalkoxy and alkylamino groups, as defined herein may be straight-chain or, when there is a sufficient number (i.e. a minimum of three) of carbon atoms, be branched-chain, and/or cyclic. Further, when there is a sufficient number (i.e. a minimum of four) of carbon atoms, such groups may also be part cyclic/acyclic. Such alkyl groups, and alkyl parts of alkoxy, alkoxyalkyl, alkoxyalkoxy and alkylamino groups, may also be saturated or, when there is a sufficient number (i.e. a minimum of two) of carbon atoms, be unsaturated. Unless otherwise specified, such groups may also be substituted by one or more halo, and especially fluoro, atoms.

For the avoidance of doubt, alkoxy and alkoxyalkoxy groups are attached to the rest of the molecule via the oxygen atom in that group, alkylamino groups are attached to the rest of the molecule via the nitrogen atom of the amino part of that group and alkoxyalkyl groups are attached to the rest of the molecule via the alkyl part of that group.

The term "halo", when used herein, includes fluoro, chloro, bromo and iodo.

Preferred ring systems comprising the substituents $Y_1$, $Y_2$, $Y_3$ and $Y_4$ include phenyl groups. For the avoidance of doubt, the ring systems in compounds of formula I that comprise the groups $Z_1$ and $Z_2$, are aromatic in nature. Preferred ring systems comprising $Z_1$ and $Z_2$ include thiazole groups and, particularly, thiophenyl groups.

In this respect, compounds of the invention may exhibit tautomerism. All tautomeric forms and mixtures thereof are included within the scope of the invention.

Compounds of the invention also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Preferred compounds of formula I include those in which:

$R^2$ represents $C_{1-3}$ alkyl, such as methyl, halo, or, especially, H;

$R^3$ represents $C_{1-3}$ alkyl, halo or, especially, H;

$Y_1, Y_2, Y_3$ and $Y_4$ all represent —CH—;

$Z_2$ represents —CH—;

$R^4$ represents $S(O)_2N(H)C(O)R^6$;

$R^5$ represents n-butyl or, particularly, iso-butyl;

$R^6$ represents n-butoxymethyl, iso-butoxy and especially, n-butoxy.

Compounds of the invention that may be mentioned include those in which, when $Y_1, Y_2, Y_3$ and $Y_4$ all represent —CH—, $Z_2$ represents —CH— and $R^5$ represents n-butyl or, particularly, iso-butyl, then $R^4$ represents —S(O)$_2$N(H)C(O)$R^6$, in which $R^6$ represents —O-iso-propyl (i.e. iso-propoxy), —O-iso-butyl (i.e. iso-butoxy), —CH$_2$—O-n-butyl (i.e. n-butoxymethyl) or, particularly, —O-n-butyl (i.e. n-butoxy).

Further compounds of the invention that may be mentioned include those in which:

$R^4$ does not represent —S(O)$_2$N(H)S(O)$_2R^6$;

$R^5$ does not represent di-$C_{1-3}$ alkylamino-$C_{1-4}$-alkyl;

$R^6$ does not represent $C_{1-3}$ alkoxy-$C_{1-6}$ alkoxy.

More preferred compounds of the invention include the compounds of the examples described hereinafter.

Compounds of formula I may be made in accordance with techniques well known to those skilled in the art, for example as described in international patent application WO 2002/096883 (or as described below).

A process for the preparation of a compound of formula I may comprise:

(i) for compounds of formula I in which $R^4$ represents —S(O)$_2$N(H)C(O)$R^6$ or —S(O)$_2$N(H)S(O)$_2R^6$, and $R^6$ is as hereinbefore defined, reaction of a compound of formula II,

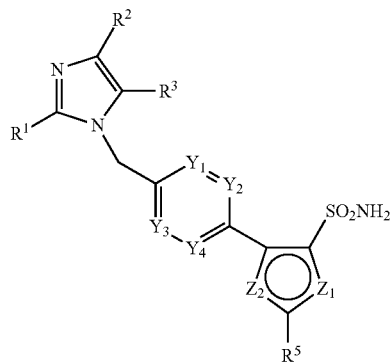

II wherein $R^1, R^2, R^3, Y_1, Y_2, Y_3, Y_4, Z_1, Z_2$ and $R^5$ are as hereinbefore defined with a compound of formula III, $$R^6GL^1 \quad \text{III}$$

wherein G represents C(O) or S(O)$_2$ (as appropriate), $L^1$ represents a suitable leaving group, such as halo (e.g. chloro or bromo) and $R^6$ is as hereinbefore to defined, for example at around room temperature or above (e.g. up to 60-70° C.) in the presence of a suitable base (e.g. pyrollidinopyridine, pyridine, triethylamine, tributylamine, trimethylamine, dimethylaminopyridine, di-iso-propylamine, 1,8-diazabicyclo[5.4.0]undec-7-ene, sodium hydroxide, or mixtures thereof) and an appropriate solvent (e.g. pyridine, dichloromethane, chloroform, tetrahydrofuran, dimethylformamide, trifluoromethylbenzene or triethylamine). Preferred base/solvent systems for compounds of formula III in which G is C(O) include pyrollidinopyridine/pyridine, pyrollidinopyridine/triethylamine, dimethylamino-pyridine/pyridine or dimethylaminopyridine/triethylamine. Preferred base/solvent systems for compounds of formula III in which G is S(O)$_2$ include NaOH/THF;

(ii) for compounds of formula I in which $R^4$ represents —S(O)$_2$N(H)C(O)$R^6$ and $R^6$ represents $C_{1-6}$ alkoxy-$C_{1-6}$-alkyl, coupling of a compound of formula II as hereinbefore defined with a compound of formula IV, $$R^{6a}CO_2H \quad \text{IV}$$

wherein $R^{6a}$ represents $C_{1-6}$ alkoxy-$C_{1-6}$-alkyl, for example under similar conditions to those described under process step (i) above, in the presence of a suitable coupling reagent (e.g. 1,1'-carbonyl-diimidazole, N,N'-dicyclohexylcarbodiimide, N,N'-disuccinimidyl carbonate, benzotriazole-1-yloxytris(dimethylamino)phosphonium hexafluorophosphate, 2-(1H-benzotriazole-1-yl)-1,1,3,3-tetramethyluronium hexafluorophosphate, benzotriazole-1-yl-oxy-tris-pyrrolidino-phosphonium hexafluorophosphate, bromo-tris-pyrrolidinophosponium hexafluorophosphate or 2-(1H-benzotriazole-1-yl)-1,1,3,3-tetramethyluronium tetrafluorocarbonate), a suitable base (as mentioned in process step (i) above) and an appropriate solvent (as mentioned in process step (i) above);

(iii) for compounds of formula I in which $R^4$ represents —C(O)N(H)S(O)$_2R^6$ and $R^6$ is as hereinbefore defined, coupling of a compound of formula V,

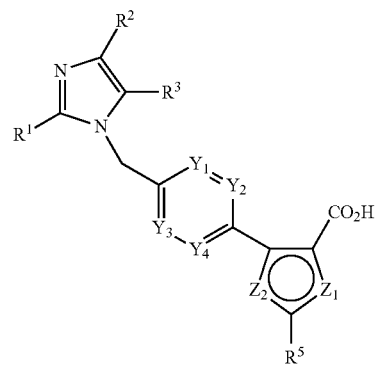

V wherein $R^1, R^2, R^3, Y_1, Y_2, Y_3, Y_4, Z_1, Z_2$ and $R^5$ are as hereinbefore defined with a compound of formula VI, $$R^6S(O)_2NH_2 \quad \text{VI}$$

wherein $R^6$ is as hereinbefore defined, for example in the presence of a suitable coupling reagent (such as those described in process step (ii) hereinbefore), and under similar reaction conditions to those described hereinbefore for preparation of compounds of formula I in which $R^6$ represents $C_{1-6}$ alkoxy-$C_{1-6}$-alkyl;

(iv) for compounds of formula I in which $R^4$ represents —C(O)N(H)S(O)$_2R^6$ and $R^6$ is as hereinbefore defined, coupling of a compound of formula VII,

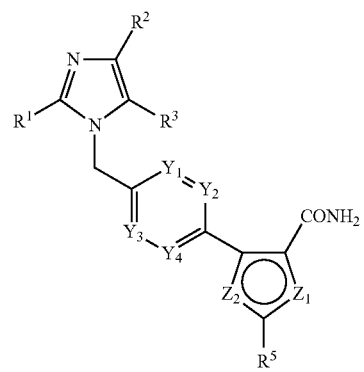

VII wherein $R^1$, $R^2$, $R^3$, $Y_1$, $Y_2$, $Y_3$, $Y_4$, $Z_1$, $Z_2$ and $R^5$ are as hereinbefore defined with a compound of formula VIII,

   VIII wherein $R^6$ is as hereinbefore defined, for example at around 50° C. in the presence of a suitable base (e.g. sodium hydride) and an appropriate organic solvent (e.g. THF);

(v) for compounds of formula I in which $R^4$ represents $-S(O)_2N(H)C(O)R^6$ and $R^6$ represents $C_{1-6}$ alkylamino, reaction of a compound of formula II as hereinbefore defined with an isocyanate compound of formula IX,

   IX wherein $R^{6b}$ is $C_{1-6}$ alkyl, for example at or around room temperature in the presence of a suitable base (e.g. sodium hydroxide or potassium hydroxide and an appropriate organic solvent (e.g. acetone or acetonitrile); or (vi) for compounds of formula I in which $R^4$ represents $-S(O)_2N(H)C(O)R^6$ and $R^6$ represents di-$C_{1-6}$ alkylamino, reaction of a corresponding compound of formula I in which $R^4$ represents $-S(O)_2N(H)C(O)R^6$ and $R^6$ represents $C_{1-6}$ alkoxy with an amine of formula X,

   X wherein $R^{6c}$ and $R^{6d}$ independently represent $C_{1-6}$ alkyl, for example at above room temperature (e.g. at between 70° C. and 100° C.) in the presence of an appropriate organic solvent (e.g. toluene).

Compounds of formula II may be prepared by reaction of a compound of formula XI,

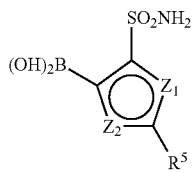   XI wherein $R^5$, $Z^1$ and $Z^2$ are as hereinbefore defined, or a N-protected derivative thereof, with a compound of formula XII,

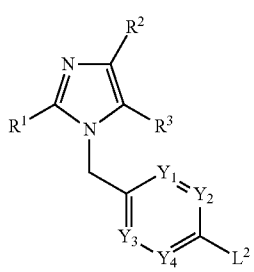   XII wherein $L^2$ represents a suitable leaving group, such as trimethylsulphonate, or halo, such as iodo or bromo, and $R^1$, $R^2$, $R^3$, $Y_1$, $Y_2$, $Y_3$ and $Y_4$ are as hereinbefore defined, for example in the presence of an appropriate coupling catalyst system (e.g. a palladium catalyst, such as $Pd(PPh_3)_4$ or $Pd(OAc)_2$/ligand (wherein the ligand may be, for example, $PPh_3$, $P(o\text{-Tol})_3$ or 1,1'-bis(diphenylphosphino)ferrocene)) and a suitable base (e.g. sodium hydroxide, sodium carbonate, potassium carbonate, cesium carbonate, triethylamine or di-iso-propylamine)), as well as a suitable solvent system (e.g. toluene, ethanol, dimethoxymethane, dimethylformamide, ethylene glycol dimethyl ether, water, dioxane or mixtures thereof). This reaction may be carried out at above room temperature (e.g. at the reflux temperature of the solvent system that is employed). If a protected version of a compound of formula XI is employed, this reaction may be followed by deprotection of the $SO_2NH$-group under standard conditions, for example as described hereinafter.

Compounds of formula II may alternatively be prepared by reaction of a compound of formula XIII,

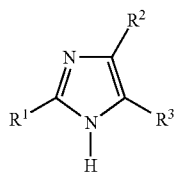   XIII wherein $R^1$, $R^2$ and $R^3$ are as hereinbefore defined with a compound of formula XIV,

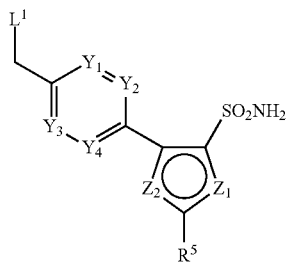   XIV wherein $Y_1$, $Y_2$, $Y_3$, $Y_4$, $Z_1$, $Z_2$, $R^5$ and $L^1$ are as hereinbefore defined ($L^1$, in particular, may represent bromo), or a N-protected derivative thereof, for example at around or below room temperature in the presence of a suitable base (e.g. potassium hydroxide) and an appropriate organic solvent (e.g. DMSO). If a protected version of a compound of formula XIV is employed, this reaction may be followed by deprotection of the $SO_2NH$-group under standard conditions, for example as described hereinafter. Further, compounds of formula II in which $Z_1$ is —S— and $Z_2$ is —CH— may be prepared in this way for example according, or analogously, to processes described in inter alia UK patent application GB 2281298.

Compounds of formula V may be prepared by oxidation of a compound of formula XV,

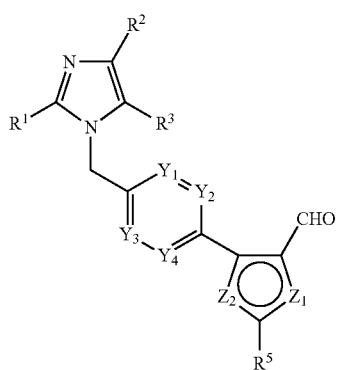   XV wherein $R^1$, $R^2$, $R^3$, $Y_1$, $Y_2$, $Y_3$, $Y_4$, $Z_1$, $Z_2$ and $R^5$ are as hereinbefore defined, for example under standard oxidation conditions in the presence of a suitable oxidising agent, such as potassium permanganate or chromium (VI) oxide.

Compounds of formula VII may be prepared by reaction of a compound of formula XII as hereinbefore defined with a compound of formula XVI,

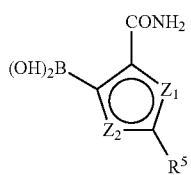

XVI wherein, $Z_1$, $Z_2$ and $R^5$ are as hereinbefore defined, or N-protected derivatives thereof, for example under similar conditions to those described hereinbefore for preparation of compounds of formula II (first process). If a protected version of a compound of formula XVI is employed, this reaction may be followed by deprotection of the NH-group under standard conditions (e.g. acid hydrolysis).

Compounds of formula XII may be prepared by standard techniques, for example by way of reaction of a compound of formula XIII as hereinbefore defined with a compound of formula XVII,

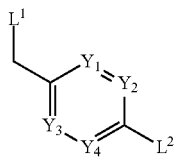

XVII wherein $Y_1$, $Y_2$, $Y_3$, $Y_4$, $L^1$ and $L^2$ are as hereinbefore defined, for example under similar conditions to those described hereinbefore in respect of preparation of compounds of formula II (second process).

Compounds of formula XIV are known in the art. For example, they may be prepared according, or analogously, to processes described in inter alia U.S. Pat. No. 5,312,820, UK patent application GB 2281298, and/or by reaction of a compound of formula XI as hereinbefore defined with a compound of formula XVIII,

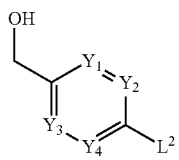

XVIII wherein $Y_1$, $Y_2$, $Y_3$, $Y_4$ and $L^2$ are as hereinbefore defined, for example under similar conditions to those described hereinbefore in respect of preparation of compounds of formula II (first process), followed by conversion of the OH group in the resultant intermediate to an appropriate leaving group, $L^1$ (e.g., in the case where $L^1$ is bromo, conversion may be carried out by reaction with $CBr_4$, for example at or around room temperature in the presence of a base (e.g. triphenylphosphine) and a suitable organic solvent (e.g. DMF)).

Compounds of formula XV may be prepared by reaction of a compound of formula XII as hereinbefore defined with a compound of formula XIX,

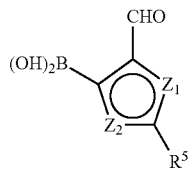

XIX wherein $Z_1$, $Z_2$ and $R^5$ are as hereinbefore defined, or a protected (at the aldehyde part) derivative thereof, for example under similar conditions to those described hereinbefore for preparation of compounds of formula II (first process). If a protected version of a compound of formula XIX is employed, this reaction may be followed by deprotection of the CHO-group under standard conditions (e.g. acid hydrolysis).

Compounds of formulae XI, XVI and XIX and protected derivatives thereof may be prepared by reaction of a corresponding compound of formula XX,

XX wherein $R^y$ represents $-S(O)_2NH_2$, $-C(O)NH_2$, $-NH_2$ or $-CHO$ (as appropriate) and $R^5$, $Z_1$ and $Z_2$ are as hereinbefore defined, or an appropriate protected derivative thereof, with a reagent system that will enable the introduction of the $-B(OH)_2$ into the appropriate ring system. Suitable reagent systems include trialkylborates (e.g. tri-iso-propylborate). Such reactions may be carried out, for example, at low temperature (e.g. between $-100°$ C. and $0°$ C., e.g. between $-80°$ C. (such as $-78°$ C.) and $-10°$ C. (such as $-20°$ C.)) in the presence of a suitable base (e.g. n-butyl lithium) and an appropriate organic solvent (e.g. THF), followed by acid hydrolysis (e.g. in the presence of dilute HCl).

Compounds of formula XX are available using known techniques. For example:
(a) Compounds of formula XX in which $R^y$ represents $-S(O)_2NH_2$, $-C(O)NH_2$ or $-CHO$, and protected derivatives thereof, may be prepared by reaction of a compound of formula XXI,

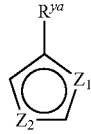

XXI wherein $R^{ya}$ represents $-S(O)_2NH_2$, $-C(O)NH_2$ or $-CHO$ and $Z_1$ and $Z_2$ are as hereinbefore defined, or a protected derivative thereof, with a compound of formula XXII, $R^5L^3$

XXII wherein L³ represents a suitable leaving group (such as toluenesulphonate, benzenesulphonate, methanesulphonate or halo, such as bromo or iodo) and $R^5$ is as hereinbefore defined, for example at below room temperature (e.g. between around −35° C. and around −85° C.), in the presence of a suitable base (e.g. n-butyl lithium) and an appropriate solvent (e.g. THF).

(b) Compounds of formula XX in which $R^y$ is —S(O)$_2$NH$_2$ and N-protected derivatives thereof, may be prepared by reaction of an appropriate compound of formula XXIII,

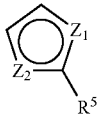

XXIII wherein $R^5$, $Z_1$ and $Z_2$ are as hereinbefore defined with an appropriate reagent for introduction of a —S(O)$_2$NH$_2$ group into the appropriate ring system (for example chlorosulphonic acid, or thionyl chloride in the presence of a suitable strong base (e.g. butyl lithium)), followed by reaction of the resultant intermediate with ammonia, or a protected derivative thereof (e.g. tert-butylamine), under conditions that are well known to those skilled in the art.

(c) Certain protected derivatives (e.g. alkyl, such as C$_{1-6}$ alkyl, for example tert-butyl, protected derivatives) of compounds of formula XX in which $R^y$ represents —C(O)NH$_2$ may be prepared by reaction of a compound of formula XXIII as hereinbefore defined, with a compound of formula XXIV, $$R^zN=C=O \qquad XXIV$$

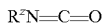

wherein $R^z$ represents an appropriate protecting group, such as an alkyl group, including C$_{1-6}$ alkyl, e.g. tert-butyl, for example at low temperature (e.g. −78° C. to around 0° C.), in the presence of a suitable base (e.g. n-butyl lithium) and an appropriate solvent (e.g. THF).

(d) Certain protected derivatives (e.g. alkyl, such as C$_{1-6}$ alkyl, for example tert-butyl, protected derivatives) of compounds of formula XX in which $R^y$ represents —C(O)NH$_2$ may also be prepared by reaction of a compound of formula XXV,

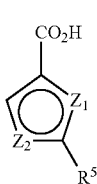

XXV wherein $R^5$, $Z_1$ and $Z_2$ are as hereinbefore defined with a protected (e.g. an (e.g. C$_{1-6}$) alkyl, such as tert-butyl-protected) derivative of ammonia (e.g. tert-butylamine) under standard coupling conditions (see, for example, those described hereinbefore for preparation of compounds of formula I (process step (iii))). Compounds of formula XXV are known in the art or may be prepared by way of standard techniques, for example oxidation of a corresponding compound of formula XX in which $R^y$ is —CHO e.g. under those conditions described hereinbefore for preparation of compounds of formula V.

Compounds mentioned herein (e.g. intermediates of formulae III, IV, VI, VIII, IX, X, XIII, XVII, XVIII, XXI, XXII, XXIII and XXIV) are either commercially available, are known in the literature, or may be obtained either by analogy with the processes described herein, or by conventional synthetic procedures, in accordance with standard techniques, from readily available starting materials using appropriate reagents and reaction conditions.

Compounds of the invention may be isolated from their reaction mixtures using conventional techniques.

It will be appreciated by those skilled in the art that, in the processes described above and hereinafter, the functional groups of intermediate compounds may need to be protected by protecting groups.

Functional groups that it is desirable to protect include sulphonamido, amido, amino and aldehyde. Suitable protecting groups for sulphonamido, amido and amino include tert-butyloxycarbonyl, benzyloxycarbonyl, 2-trimethylsilylethoxycarbonyl (Teoc) or tert-butyl. Suitable protecting groups for aldehyde include alcohols, such as methanol or ethanol, and diols, such as 1,3-propanediol or, preferably, 1,2-ethanediol (so forming a cyclic acetal).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques (e.g. using trifluoroacetic acid, sulfuric acid, toluenesulfonic acid or boron trichloride).

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 3$^{rd}$ edition, T. W. Greene & P. G. M. Wutz, Wiley-Interscience (1999).

Medical and Pharmaceutical Uses

Compounds of the invention are useful because they possess pharmacological activity. In particular, compounds of the invention are agonists of AngII, more particularly, are agonists of the AT2 receptor, and, especially, are selective agonists of that sub-receptor.

It has now been found that compounds of the invention (i.e. AT2 receptor agonists) are useful in the treatment of conditions (spinal chord injury, e.g. caused by trauma) in which reinnervation and/or remyelination is desired or required. This may be due to the fact that the compounds of the invention (i.e. AT2 receptor agonists) increase the expression of various neurotrophic factors (particularly brain-derived neurotrophic factor, BDNF) or due to the fact that they have the same effect as increasing the expression of those neurotrophic factors (by which we mean that they produce the same end result, e.g. by forming the same molecules and/or ultimately having the same therapeutic effect), and therefore promoting reinnervation and/or remyelination (thereby being useful in the treatment of spinal chord injury).

Spinal chord injury (e.g. caused by trauma) is a specific medical conditions in which reinnervation or remyelination may be desired or required and it has been found that the compounds of the invention (i.e. the AT2 receptor agonist) show unexpectedly efficacy in treating spinal chord injury (as shown by the examples).

Spinal cord injuries may be caused by tumours, ischemia resulting from occlusion of spinal blood vessels, developmental disorders, neurodegenerative diseases, demyelinative diseases, transverse myelitis, vascular malformations or, particularly, trauma such as general accidents, automobile crashes, falls, gunshots, war injuries, etc.

The compounds of the invention are therefore indicated in the therapeutic treatment of the above conditions, particularly spinal chord injury caused by trauma.

According to a further aspect of the present invention, there is provided a method of treatment of a spinal cord injury (in which reinnervation and/or remyelination is desired or required), and/or a spinal cord injury where AT2 receptors are expressed and their stimulation is desired or required, which method comprises administration of a therapeutically effective amount of a compound of the invention (or a pharmaceutically acceptable salt thereof) to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in a pharmaceutically acceptable dosage form.

The compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, in admixture with a pharmaceutically acceptable adjuvant, diluent or carrier, for use in the treatment of spinal cord injury (as defined herein).

Compounds of the invention may also be administered in combination with other AT2 agonists that are known in the art, as well as in combination with AT1 receptor antagonists that are known in the art, such as losartan, or in combination with an inhibitor of angiotensin converting enzyme (ACE). Such combinations may therefore be useful in the treatment of spinal cord injury (as defined herein).

According to a further aspect of the invention, there is provided a combination product comprising:
(A) an AT2 receptor agonist or a compound capable of stimulating AT2 receptors; and
(B) an AT1 receptor antagonist, or an ACE inhibitor,
wherein each of components (A) and (B) is formulated in admixture with a pharmaceutically-acceptable adjuvant, diluent or carrier, for use in the treatment of spinal cord injury (as defined herein).

Such combination products provide for the administration of an AT2 receptor agonist or a compound capable of stimulating AT2 receptors (as defined herein), in conjunction with an AT1 receptor antagonist or an ACE inhibitor, and may thus be presented either as separate formulations, wherein at least one of those formulations comprises an AT2 receptor agonist or a compound capable of stimulating AT2 receptors (as defined herein, e.g. a compound of formula I, or a pharmaceutically acceptable salt thereof), and at least one comprises AT1 receptor antagonist or ACE inhibitor, or may be presented (i.e. formulated) as a combined preparation (i.e. presented as a single formulation including an AT2 receptor agonist or a compound capable of stimulating AT2 receptors together with either an AT1 receptor antagonist or an ACE inhibitor).

Thus, there is further provided:
(1) a pharmaceutical formulation including an AT2 receptor agonist or a compound capable of stimulating AT2 receptors (e.g. a compound of the invention, i.e. a compound of formula I or a pharmaceutically acceptable salt thereof) and an AT1 receptor antagonist, or an ACE inhibitor, in admixture with a pharmaceutically-acceptable adjuvant, diluent or carrier, for use in the treatment of spinal cord injury; and
(2) a kit of parts comprising components:
(a) a pharmaceutical formulation including an AT2 receptor agonist or a compound capable of stimulating AT2 receptors (e.g. a compound of the invention, i.e. a compound of formula I or a pharmaceutically acceptable salt thereof), in admixture with a pharmaceutically-acceptable adjuvant, diluent or carrier; and
(b) a pharmaceutical formulation including an AT1 receptor antagonist, or an ACE inhibitor, in admixture with a pharmaceutically-acceptable adjuvant, diluent or carrier,
which components (a) and (b) are each provided in a form that is suitable for administration in conjunction with the other, for use in the treatment of spinal cord injury.

Depending upon the patient to be treated and the route of administration, the compounds of the invention may be administered at varying doses.

Although doses will vary from patient to patient, suitable daily doses are in the range of about 1 to 1000 mg per patient, administered in single or multiple doses. More preferred daily doses are in the range 2.5 to 250 mg per patient.

Individual doses of compounds of the invention may be in the range 1 to 100 mg.

In any event, the physician, or the skilled person, will be able to determine the actual dosage which will be most suitable for an individual patient, which is likely to vary with the condition that is to be treated, as well as the age, weight, sex and response of the particular patient to be treated. The abovementioned dosages are exemplary of the average case; there can, of course, be individual instances where higher or lower dosage ranges are merited, and such are within the scope of this invention.

Compounds of the invention have the advantage that they bind selectively to, and exhibit agonist activity at, the AT2 receptor. By compounds which "bind selectively" to the AT2 receptor, we include that the affinity ratio for the relevant compound (AT2:AT1) is at least 5:1, preferably at least 10:1 and more preferably at least 20:1. Consequently, the compounds of the invention are useful in the treatment of spinal chord injury as described herein.

The compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art.

The (greater) efficacy of the compounds of the invention (i.e. the AT2 receptor agonists) may be measured on an absolute or a relative scale. As may be shown by the examples, with reference to the figures, the efficacy may be based on a "Basso Score". It is known in the art that a Basso Score of greater than 0.5 shows that there is efficacy in the treatment of spinal cord injury. Unexpectedly, the compounds of the invention (i.e. the AT2 receptor agonists) showed a Basso Score of far greater than 0.5 (see e.g. figures), which could not have been previously predicted (e.g. from in vitro results, etc).

Preferred non-limiting examples which embody certain aspects of the invention will now be described with reference to the following figures.

FIGURES

FIG. 1 which shows the Basso Mouse Score for Balb/C mice treated once daily with vehicle or the compound of Example 1(i).

Figure 2:
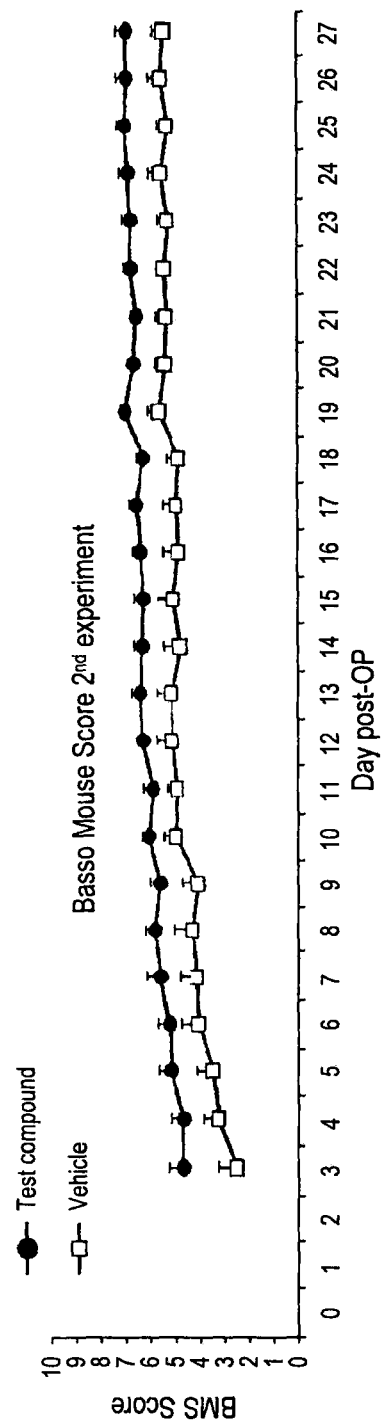

FIG. 2 which shows the Basso Mouse Score for Balb/C mice treated with the test compound administered either intraperitoneally or via a gel placed at the site of injury.

Figure 3:
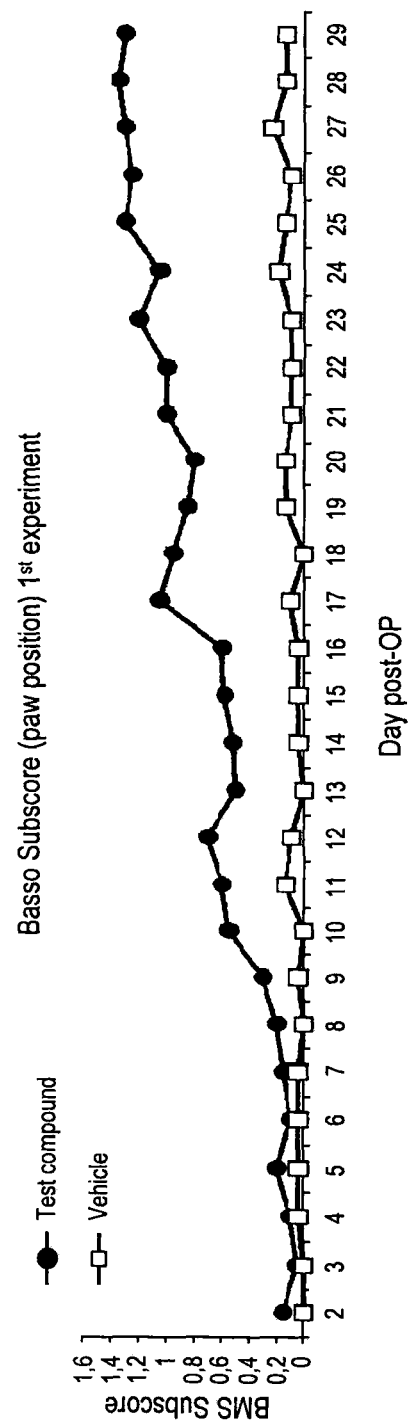

FIG. 3 which shows the Basso subscore for paw position for Balb/C mice treated once daily with vehicle or the compound of Example 1(i).

Figure 4:
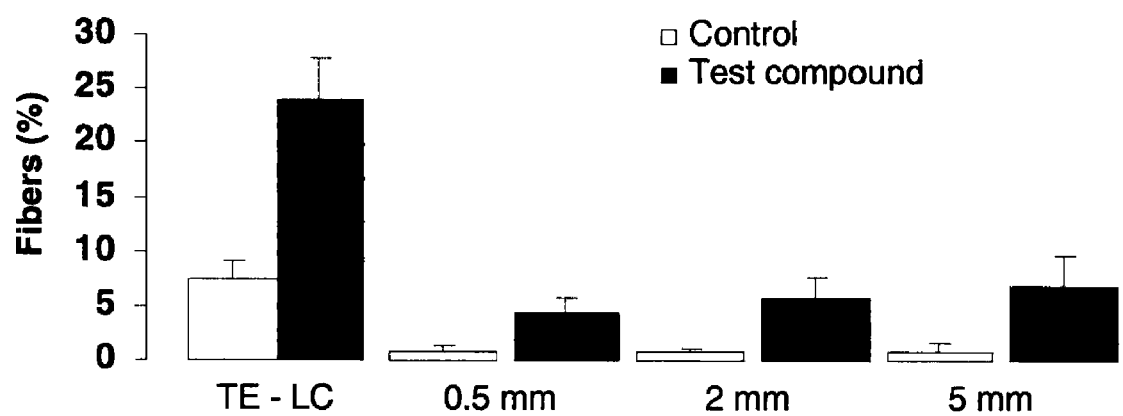

FIG. 4 which shows a graph in which bars represent the percentage of nerve fibres in the area between the end of the corticospinal tract and the lesion centre (TE-LC) and in areas at various distances distal to the lesion centre (e.g. 0.5 mm from LC). TE refers to the end of the corticospinal tract. LC refers to the lesion centre. The test compound was the compound of Example 1(i).

Figure 5A:
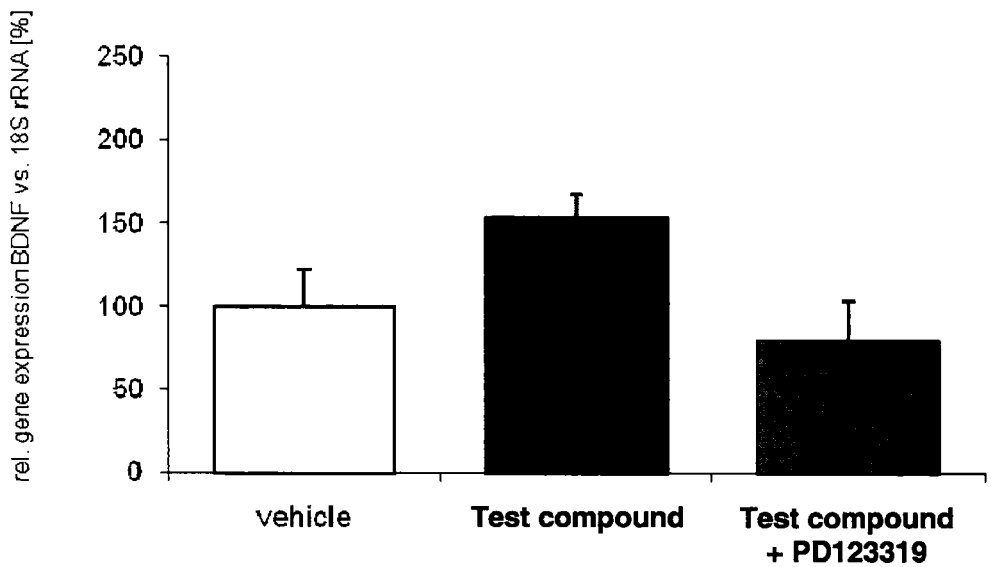
Figure 5B:
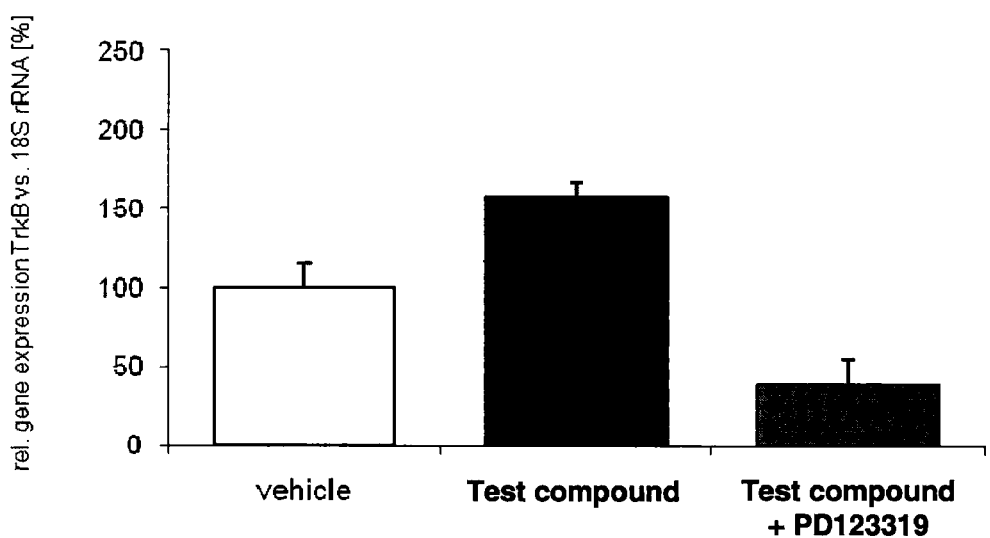

FIGS. 5a and 5b which show the relative genetic expression of BDNF (FIG. 5a) or TrkB (FIG. 5b) in primary mouse neurons following treatment with the vehicle, the compound of Example 1(i), or a combination of the compound of Example 1(i) and an AT2 receptor antagonist PD123319.

Figure 6A:
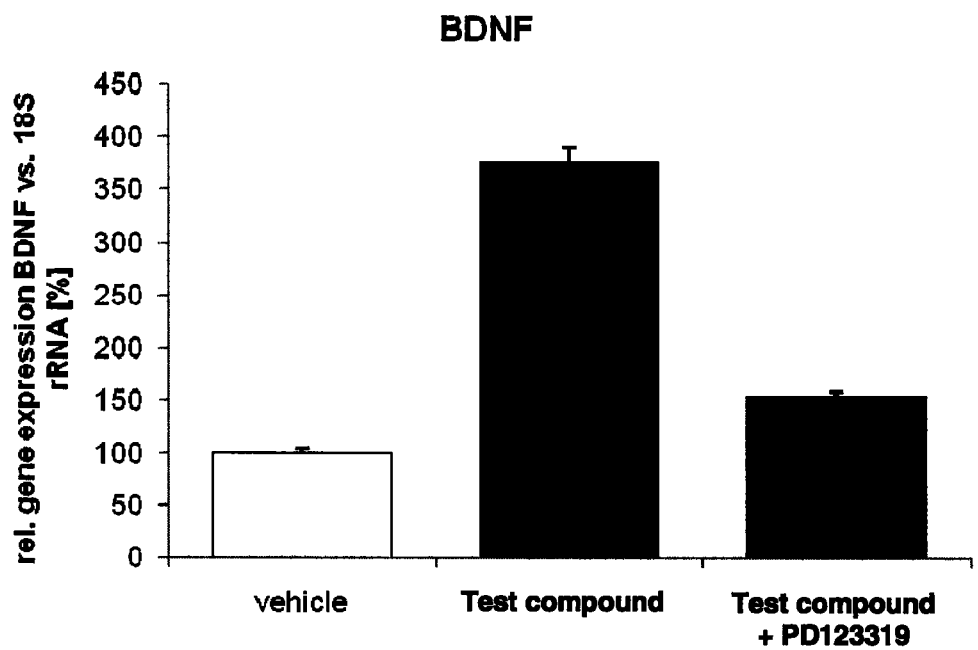
Figure 6B:
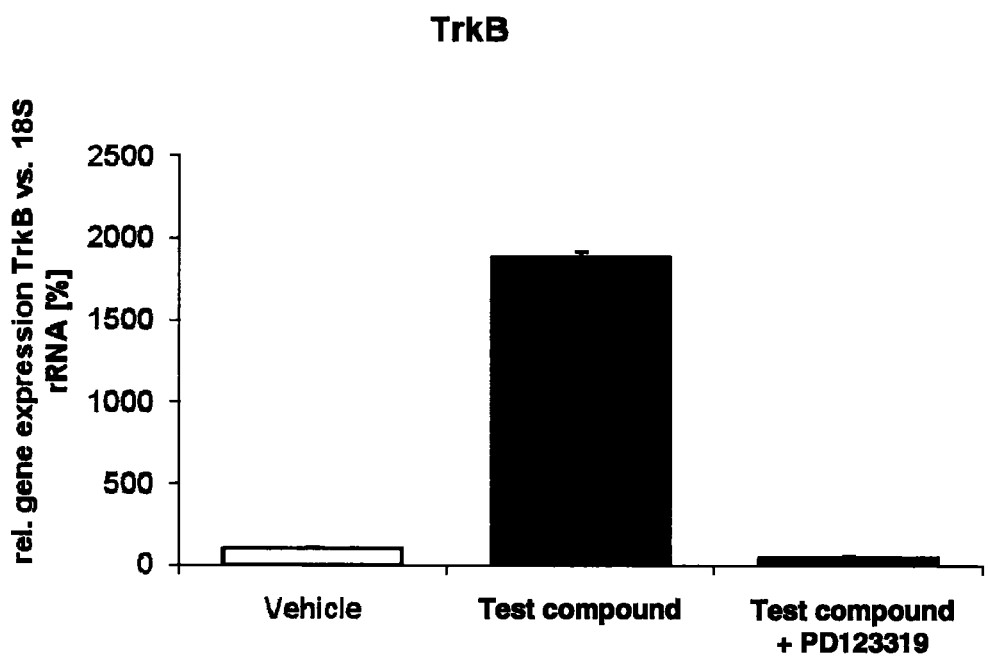

FIGS. 6a and 6b which show the relative genetic expression of BDNF (FIG. 6a) or TrkB (FIG. 6b) in primary mouse astrocytes following treatment with the vehicle, the compound of Example 1(i), or a combination of the compound of Example 1(i) and an AT2 receptor antagonist PD123319.

Figure 7:
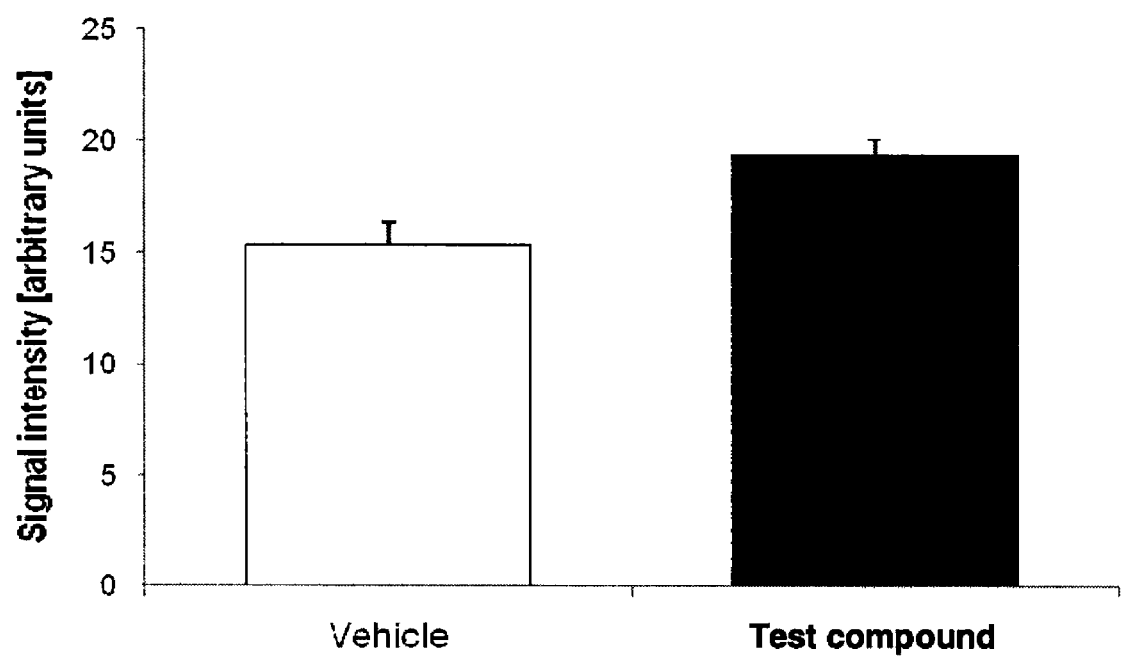

FIG. 7 which shows the results of a quantitative image analysis for TrkB expression in injured spinal cords in mice. The data presented as the heights of the bars in the chart are presented in arbitrary units of signal intensity. Greater TrkB expression leads to increased staining and an increased signal intensity in the image analysis. The test compound was the compound of Example 1(i).

Figure 8:
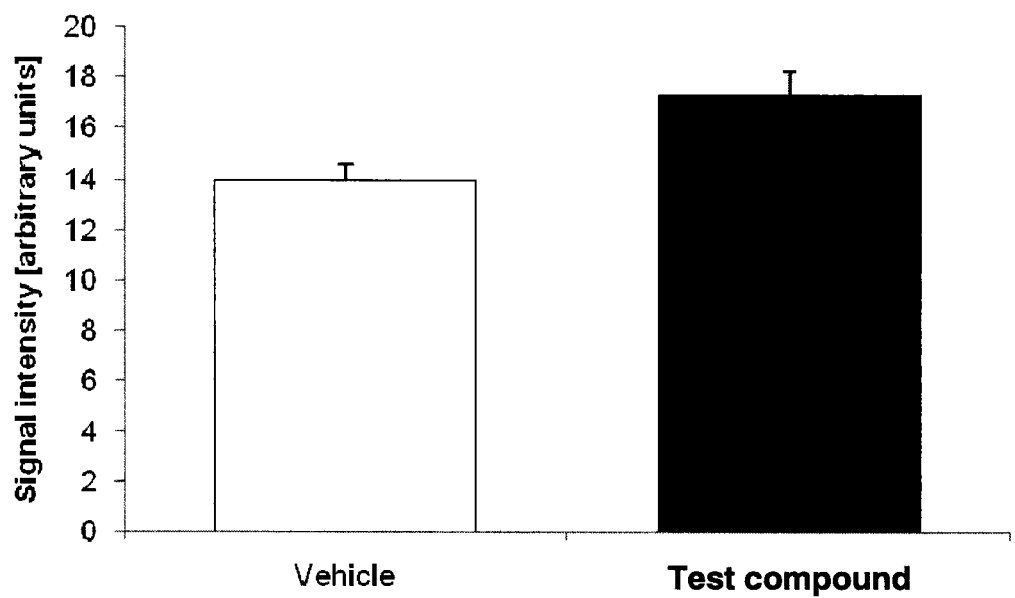

FIG. 8 which shows the results of a quantitative analysis of the number of viable neurons at the site of injury of spinal cords derived from treated mice by Nissl staining. Where quantification of signal intensity reveals that there is a significant increase in Nissl positive cells for animals receiving a certain treatment, this indicates a higher number of viable neurons at the site of spinal cord injury after that treatment. The test compound was the compound of Example 1(i).

BIOLOGICAL TESTS

In studies of spinal cord injury in mice, the recovery of the mice in the studies may be monitored and quantified using the Basso Mouse Scale (Basso D. M., et al., *Journal of Neurotrauma*, Volume 23, No. 5, 635-659 (2006), the entirety of which is hereby incorporated by reference). Using this method, each mouse in such studies may be awarded a score based on the criteria outlined in Table 1 and FIG. 1 of Basso et al., supra,

EXAMPLES

Example 1

The following compounds of the invention were prepared by methods described herein or by the methods of international patent application no. WO 2002/096883, which document is hereby incorporated by reference.
(i) N-Butyloxycarbonyl-3-(4-imidazol-1-ylmethylphenyl)-5-iso-butylthiophene-2-sulfonamide (this compound is particularly preferred);
(ii) N-iso-Butyloxycarbonyl-3-(4-imidazol-1-ylmethylphenyl)-5-iso-butyl-thiophene-2-sulfonamide;
(iii) N-iso-Propyloxycarbonyl-3-(4-imidazol-1-ylmethylphenyl)-5-iso-butyl-thiophene-2-sulfonamide;
(iv) N-(Butoxyacetyl)-3-(4-imidazol-1-ylmethylphenyl)-5-iso-butylthiophene-2-sulfonamide;
(v) N-Butyloxycarbonyl-3-(4-imidazol-1-ylmethylphenyl)-5-butylthiophene-2-sulfonamide;
(vi) N-(Butylamino)carbonyl-3-(4-imidazol-1-ylmethylphenyl)-5-iso-butyl-thiophene-2-sulfonamide;
(vii) N-Butylsulfonyl-3-(4-imidazol-1-ylmethylphenyl)-5-iso-butylthiophene-2-sulfonamide;
(viii) N-Butylsulfonyl-3-(4-imidazol-1-ylmethylphenyl)-5-iso-butylthiophene-2-carboxamide;
(ix) N-(2-methoxyethyloxy)carbonyl-3-(4-imidazol-1-ylmethylphenyl)-5-iso-butylthiophene-2-sulfonamide;
(x) N-ethyloxycarbonyl-3-(4-imidazol-1-ylmethylphenyl)-5-iso-butylthiophene-2-sulfonamide;
(xi) N-tert-butyloxycarbonyl-3-(4-imidazol-1-ylmethylphenyl)-5-iso-butyl-thiophene-2-sulfonamide;
(xii) N-butyloxycarbonyl-3-[4-(4-methylimidazol-1-ylmethyl)phenyl]-5-iso-butylthiophene-2-sulfonamide;
(xiii) N—(N-butyl-N-methylamino)carbonyl-3-(4-imidazol-1-ylmethyl-phenyl)-5-iso-butylthiophene-2-sulfonamide; and
(xiv) N-butyloxycarbonyl-3-(4-imidazol-1-ylmethylphenyl)-5-(2-methoxy-ethyl)thiophene-2-sulfonamide.

Example 2

Spinal Cord Contusion Injury

Spinal cord injury and cortical spinal tract (CST) tracing were performed as described in (Boato et al. 2010). Briefly, Balb/C mice (20-24 g; 9- to 11-weeks-old) had a dorsal laminectomy at thoracic level (T8), followed by a contusion lesion with a modified SPI Correx Tension/Compression Gage (Penn Tool, Maplewood, N.J.) for controlled compression of the mouse spinal cord for 1 second at 20 cN. A gelfoam patch containing 1 µM the compound of Example 1(i) was then placed on top of the perforated dura (only in the second experiment, see Example 3), the muscles were sutured and the back skin closed with wound clips. Recovery of function after SCI was determined by scoring the locomotor hindlimb performance in the open field with the BMS, a 0-9 rating system based on the BBB scale and specifically designed for the mouse (Basso D. M., et al., *Journal of Neurotrauma*, Volume 23, No. 5, 635-659 (2006)). Under blind conditions, investigator evaluated the mice over a 4-min time period daily. Before surgery, animals were acclimated to the open field and to handling to prevent fear and/or stress behaviours that could bias the locomotor assessment.

Animals treated with the compound of Example 1(i) presented with significantly reduced neurological deficits when compared to controls at the very beginning of the observational period (day 2 and 3) and from day 9 until the end of the study (see FIG. 1). Animals treated with the compound of Example 1(i) scored approximately 1.5 points better on the Basso Mouse Scale than vehicle treated mice.

Example 3

As part of the study detailed in Example 2, two groups of mice were treated with the compound of Example 1(i) via different routes: systemically (via i.p.) or in a gel placed at the site of injury. The neurological outcome (scored using the BMS) in the treated mice showed no statistically significant difference between the mice treated via these different routes (see FIG. 2).

Example 4

As a further part of the study detailed in Example 2, analysis was performed for a key subscore of the BMS for neurological deficits caused by spinal cord injury: paw position of hindlimbs. Animals treated with the compound of Example 1(i) showed a continuous recovery which was almost completely absent in vehicle treated mice (see FIG. 3). The increase in this subscore by treatment with the compound of Example 1(i) was statistically significant from day 7 until the end of the observational period.

Example 5

Cortical Spinal Tract Tracing

To anterogradely label the CST, 2 µl of biotinylated dextran amine (10% BDA) were then injected into the motor cortex. BDA-positive CST nerve fibres were visualized by 3,3'-diaminobenzidine staining and counted cranial and caudal to the lesion in serial sections and normalized to the number of labelled fibres in the dorsoventral diameter of the CST in cross sections at T4.

The bars in FIG. 2 represent the percentage of nerve fibres in the area between the end of the CST and the lesion centre (TE-LC) and in the area 0.1, 0.2 or 0.5 mm distal to the lesion centre (0.1, 0.2 or 0.5 mm from LC).

The potential for administration of the compound of Example 1(i) to mice to lead to regeneration of axonal fibres and bridging of the site of injury by reinnervation, following spinal cord injury, was examined. This involved tracking motor neurons by injection of BDA-labelled dextran into the motor cortex. Quantification of these axons revealed that their number was significantly increased in animals treated with the compound of Example 1(i) when compared to controls (see FIG. 4).

Example 6

Estimation of BDNF and TrkB mRNA Expression by RT-qPCR in Murine Primary Neurons Primary neurons were isolated from brains of E15 mouse embryos.

Total RNA from cells was extracted using NucleoSpin RNA II extraction kit including DNAse treatment to digest genomic DNA (Macherey & Nagel, Düren, Germany).

RNA concentration was measured spectrophotometrically at a wavelength of 260 nm. Purity was assessed by the quotient 260/280 nm.

250 ng of cell-derived mRNA were reverse transcribed into complementary DNA using moloney murine leukaemia virus (M-MLV) reverse transcriptase, 5× M-MLV buffer, deoxy-NTPs, random primers and RNasin (reagents from Promega, Mannheim, Germany) at 37° C. for 60 min. In order to control for genomic DNA contaminations, RNA was additionally transcribed in the absence of M-MLV reverse transcriptase (RT minus control).

To measure gene expression, the transcribed cDNA was amplified by quantitative real-time PCR (Stratagen MX Pro, Agilent Technologies Sales & Services GmbH & Co. KG, Waldbronn, Germany) in a final volume of 25 µl with the specific primers in commercial Power SYBR Green Master Mix (Applied Biosystems, Foster City, USA). Expression values were normalized against 18SrRNA expression.

All PCR primers were purchased from Operon Biotechnologies (Köln, Germany). The amplification protocol using the Power SYBR Green PCR Mix was as follows: one cycle at 95° C. for 10 min followed by 40 cycles at 95° C. for 15 s, at 60° C. for 1 min and at 72° C. for 30 s followed by a dissociation curve ranging from 55° C. to 95° C. Data analysis was performed according to the ΔΔCT method.

The production of mRNA encoding BDNF and its receptor TrkB was significantly increased following treatment with the compound of Example 1(i) in primary neurons (see FIGS. 5a and 5b). All effects induced by the compound of Example 1(i) described here were completely blocked by the specific AT2R-antagonist PD123319 revealing AT2R-specificity.

Example 7

Estimation of BDNF and TrkB mRNA Expression by RT-qPCR in Murine Primary Astrocytes Primary astrocytes were isolated from brains of 2 day old mouse puppies as described in Thöne-Reineke at al., 2008. RNA isolation and amplification was performed as described above.

Astrocytes are critically involved in CNS homeostasis, injury and regeneration. By synthesising and secreting neurotrophins, they are able to protect themselves and adjacent neurons. It was found that the compound of Example 1(i) (at $10^{-6}$M) induced expression of BDNF and its high affinity receptor TrkB in primary mouse astrocytes (see FIGS. 6a and 6b). All effects induced by the compound of Example 1(i) on astrocytes were abrogated by co-treatment with the selective AT2R-antagonist PD123319.

Example 8

Immunohistochemical Stainings of Spinal Cords for TrkB

Animal tissues were fixated by transcardial perfusion with normal saline followed by ice-cold 4% paraformaldehyde in 0.1 M phosphate-buffered saline. After perfusion, spinal cords were dissected and post-fixed overnight in the same fixative. The next day, the tissues were embedded in Jung-Tissue Freezing Medium (Leica Microsystems Nussloh, Germany) and cut longitudinally along the horizontal plane (40 µm thickness) into six series using a freezing microtome.

For immunostaining, samples were preincubated with 10% normal goat serum dissolved in PBS containing 0.5% Triton X-100 for 30 minutes at room temperature (RT). Incubation with primary antibody (Santa Cruz) was carried out overnight at 4° C. Following repeated washing steps with PBS, secondary antibodies (Jackson ImmunoResearch Laboratories) were applied for 2 hours at RT. After removal of unbound antibodies, sections were mounted.

For measurement of signal intensity six sections per animal containing the lesion center were analyzed. Micrographs were made in 15 rectangular boxes along the spinal cord covering the lesion and surrounding area. Using ImageJ software (NIH) pictures were converted into the 8-Bit greyscale and the signal intensity for each box was evaluated.

The immunoreactivity patterns of TrkB in longitudinal sections of spinal cords from vehicle-treated or test compound-treated mice were investigated. Image analysis used to quantify TrkB signal intensity revealed that TrkB immunoreactivity was strongly increased after a 4 week treatment with the compound of Example 1(i) not only within the area of injury, but also in the peri-lesional tissue (see FIG. 7).

Example 9

Histochemical Stainings of Spinal Cords for Nissl

Animals were fixated as described above.

For staining of viable neurons the NeuroTrace® 500/525 green fluorescent Nissl stain (Invitrogen) was used. Briefly, after rehydration tissue slices were permeabilized in PBS containing 0.1% Triton X-100 for 10 minutes at room temperature. After washing NeuroTrace solution (100 fold diluted in PBS) was applied to the sections and incubated for 20 minutes at room temperature. After washing, samples were mounted for microscopy.

For measurement of signal intensity six sections per animal containing the lesion centre were analyzed. Micrographs were made in 15 rectangular boxes along the spinal cord covering the lesion and surrounding area. Using ImageJ software (NIH) pictures were converted into the 8-Bit grayscale and the signal intensity for each box was evaluated.

The number of viable neurons at the site of injury of spinal cords derived from vehicle- or test compound-treated mice was analysed by Nissl staining. Quantification of signal intensity revealed that there was a significant increase in Nissl positive cells in test compound- versus vehicle-treated animals indicating a higher number of viable neurons at the site of spinal cord injury after treatment with the compound of Example 1(i) (see FIG. 8).

The invention claimed is:

1. A method of treating spinal cord injury, comprising administering a compound which is an AT2 receptor agonist that binds selectively to the AT2 receptor, or a pharmaceutically acceptable salt thereof, to a patient in need of such therapy.

2. A method of treating spinal cord injury, comprising administering a compound which is capable of stimulating AT2 receptors, or a pharmaceutically acceptable salt thereof, to a patient in need of such therapy.

3. The method according to claim 1, wherein the compound is a compound of formula I,

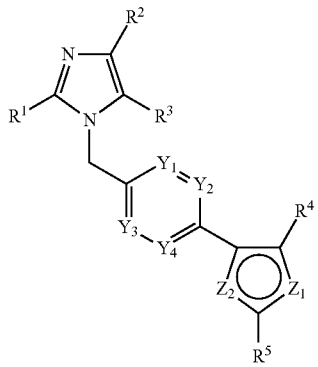

I wherein
$R^1$ represents H;
$R^2$ and $R^3$ independently represent H, $C_{1-6}$ alkyl, $C_{1-6}$ alkoxy, $C_{1-6}$ alkoxy-$C_{1-6}$-alkyl or halo;
$Y_1$, $Y_2$, $Y_3$ and $Y_4$ independently represent —CH— or —CF—;
$Z_1$ represents —S—;
$Z_2$ represents —CH— or —N—;
$R^4$ represents —S(O)$_2$N(H)C(O)R$^6$, —S(O)$_2$N(H)S(O)$_2$R$^6$, or —C(O)N(H)S(O)$_2$R$^6$;
$R^5$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl; and
$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino;
or a pharmaceutically-acceptable salt thereof.

4. The method according to claim 3, wherein $R^2$ represents $C_{1-3}$ alkyl, halo or H.

5. The method according to claim 3, wherein $R^3$ represents $C_{1-3}$ alkyl, halo or H.

6. The method according to claim 3, wherein $R^2$ and $R^3$ independently represent H.

7. The method according to claim 3, wherein $Y_1$, $Y_2$, $Y_3$ and $Y_4$ all represent —CH—.

8. The method according to claim 3, wherein $Z_2$ represents —CH—.

9. The method according to claim 3, wherein $R^4$ represents —S(O)$_2$N(H)C(O)R$^6$.

10. The method according to claim 3, wherein $R^5$ represents iso-butyl.

11. The method according to claim 3, wherein $R^6$ represents n-butoxy.

12. The method according to claim 1, wherein the compound is:
N-Butyloxycarbonyl-3-(4-imidazol-1-ylmethylphenyl)-5-iso-butylthiophene-2-sulfonamide;
N-iso-butyloxycarbonyl-3-(4-imidazol-1-ylmethylphenyl)-5-iso-butyl-thiophene-2-sulfonamide;
N-iso-propyloxycarbonyl-3-(4-imidazol-1-ylmethylphenyl)-5-iso-butyl-thiophene-2-sulfonamide;
N-(butoxyacetyl)-3-(4-imidazol-1-ylmethylphenyl)-5-iso-butylthiophene-2-sulfonamide;
N-butyloxycarbonyl-3-(4-imidazol-1-ylmethylphenyl)-5-butylthiophene-2-sulfonamide,
N-(butylamino)carbonyl-3-(4-imidazol-1-ylmethylphenyl)-5-iso-butyl-thiophene-2-sulfonamide;
N-butylsulfonyl-3-(4-imidazol-1-ylmethylphenyl)-5-iso-butylthiophene-2-sulfonamide;
N-butylsulfonyl-3-(4-imidazol-1-ylmethylphenyl)-5-iso-butylthiophene-2-carboxamide;
N-(2-methoxyethyloxy)carbonyl-3-(4-imidazol-1-ylmethylphenyl)-5-iso-butylthiophene-2-sulfonamide;
N-ethyloxycarbonyl-3-(4-imidazol-1-ylmethylphenyl)-5-iso-butylthiophene-2-sulfonamide;
N-tert-butyloxycarbonyl-3-(4-imidazol-1-ylmethylphenyl)-5-iso-butyl-thiophene-2-sulfonamide;
N-butyloxycarbonyl-3-[4-(4-methylimidazol-1-ylmethyl)phenyl]-5-iso-butylthiophene-2-sulfonamide;
N—(N-butyl-N-methylamino)carbonyl-3-(4-imidazol-1-ylmethylphenyl)-5-iso-butylthiophene-2-sulfonamide; or
N-butyloxycarbonyl-3-(4-imidazol-1-ylmethylphenyl)-5-(2-methoxyethyl)-thiophene-2-sulfonamide.

13. A method of treating a spinal cord injury comprising administering a pharmaceutical formulation including a compound which is an AT2 receptor agonist that binds selectively to the AT2 receptor, or a pharmaceutically acceptable salt thereof, in admixture with a pharmaceutically acceptable adjuvant, diluent or carrier to a patient in need of such therapy.

14. The method according to claim 13, wherein the formulation also includes an AT1 receptor antagonist.

15. The method of claim 13, wherein the formulation comprises the components:
- (a) a pharmaceutical formulation including a compound which is an AT2 receptor agonist that binds selectively to the AT2 receptor, or a pharmaceutically acceptable salt thereof, in admixture with a pharmaceutically-acceptable adjuvant, diluent or carrier; and
- (b) a pharmaceutical formulation including an AT1 receptor antagonist, in admixture with a pharmaceutically-acceptable adjuvant, diluent or carrier, which components (a) and (b) are each provided in a form that is suitable for administration in conjunction with the other, for use in the treatment of spinal cord injury.

16. The method of claim 13, wherein the formulation also includes an angiotensin converting enzyme inhibitor.

17. The method of claim 13, wherein the formulation comprises the components:
- (a) a pharmaceutical formulation including a compound which is an AT2 receptor agonist that binds selectively to the AT2 receptor, or a pharmaceutically acceptable salt thereof, in admixture with a pharmaceutically-acceptable adjuvant, diluent or carrier; and
- (b) a pharmaceutical formulation including an angiotensin converting enzyme inhibitor, in admixture with a pharmaceutically-acceptable adjuvant, diluent or carrier, which components (a) and (b) are each provided in a form that is suitable for administration in conjunction with the other, for use in the treatment of spinal cord injury.

18. The method according to claim 1, wherein the spinal cord injury is caused by trauma.

* * * * *